United States Patent

Lecuyer

[11] Patent Number: 6,093,187
[45] Date of Patent: Jul. 25, 2000

[54] CATHETER FOR NEUROSURGERY

[75] Inventor: Alain Lecuyer, Grasse, France

[73] Assignee: Elekta Implants S.A., Sophia Antipolis, France

[21] Appl. No.: 09/050,372

[22] Filed: Mar. 31, 1998

[30] Foreign Application Priority Data

Apr. 3, 1997 [FR] France ................................ 97 04061

[51] Int. Cl.[7] .................................................. A61B 18/14
[52] U.S. Cl. ................................ 606/45; 606/49; 606/192
[58] Field of Search .......................... 606/41, 45, 48–50, 606/192, 194; 607/99

[56] References Cited

U.S. PATENT DOCUMENTS 5,207,684  5/1993  Nobles .
5,364,393  11/1994  Auth et al. ................................ 606/45
5,514,131  5/1996  Edwards et al. .
5,571,088  11/1996  Lennox et al. .
5,628,746  5/1997  Clayman ................................... 606/45
5,700,262  12/1997  Acosta et al. ............................. 606/50

FOREIGN PATENT DOCUMENTS 2145932  4/1985  United Kingdom .

*Primary Examiner*—Lee S. Cohen
*Attorney, Agent, or Firm*—Dennison, Scheiner, Schultz & Wakeman

[57] ABSTRACT

A catheter for neurosurgery including a tubular body (1), on whose end is mounted a dilating balloon (5), the body being equipped for connection to a device inflating the balloon. The body internally includes an electrical feed wire (11) for an electrocautery tip disposed on the far side of the balloon.

2 Claims, 1 Drawing Sheet

CATHETER FOR NEUROSURGERY

BACKGROUND OF THE INVENTION

The present invention relates to a catheter for neurosurgery.

There are operations known in neurosurgery during which it is necessary to pierce a membrane. This may involve, for example, the piercing of the floor of the third cerebral ventricle in the treatment of hydrocephalus.

At present, these operations are performed in two stages. In a first stage, the membrane is opened, for example using an electrocautery, which is then withdrawn. In its place, a balloon catheter is inserted and inflated so as to dilate the opening.

A procedure of this type results, first of all, in a loss of time, which is always prejudicial during an operation. Furthermore, it can also produce an outflow of cephalorachidian fluid during the withdrawal of the electrocautery.

SUMMARY OF THE INVENTION

The object of the present invention is to eliminate these drawbacks.

To this end, the subject of the invention is a catheter for neurosurgery, characterized in that it comprises a tubular body on the end of which is mounted a dilating balloon, which body is equipped to be connected to means for inflating the balloon, and moreover internally comprises an electrical feed wire for an electrocautery tip located disposed on the far side of the balloon.

Thus, the tubular body of the catheter of the invention fulfills two functions. First of all, it serves as a conduit for the fluid that inflates the balloon. Secondly, it forms a sheath for the feed wire of the electrocautery tip.

The piercing of the membrane in this case is carried out in a single operation. Once the catheter is positioned with the electrocautery tip in contact with the membrane to be pierced, this tip is energized, thus producing an opening in the membrane. The catheter is then pushed slightly inward so as to partially insert the balloon into the opening. Lastly, this balloon is inflated in order to dilate the opening, after which the catheter is withdrawn.

In one particular embodiment, the end of the body coaxially supports a metal tube to whose end the electrocautery tip is welded, and to which the feed wire is electrically connected, the balloon being mounted around the metal tube, whose wall is perforated so as to allow the balloon to be inflated.

In another particular embodiment, the balloon has an elongated shape, and comprises in its center part a restriction of its diameter, which prevents it from slipping to one side of the opening or the other during its inflation.

BRIEF DESCRIPTION OF THE DRAWING

The sole drawing FIGURE is a partially sectional side view of a catheter according to the invention.

DESCRIPTION OF THE PREFERRED EMBODIMENT

Figure 1:
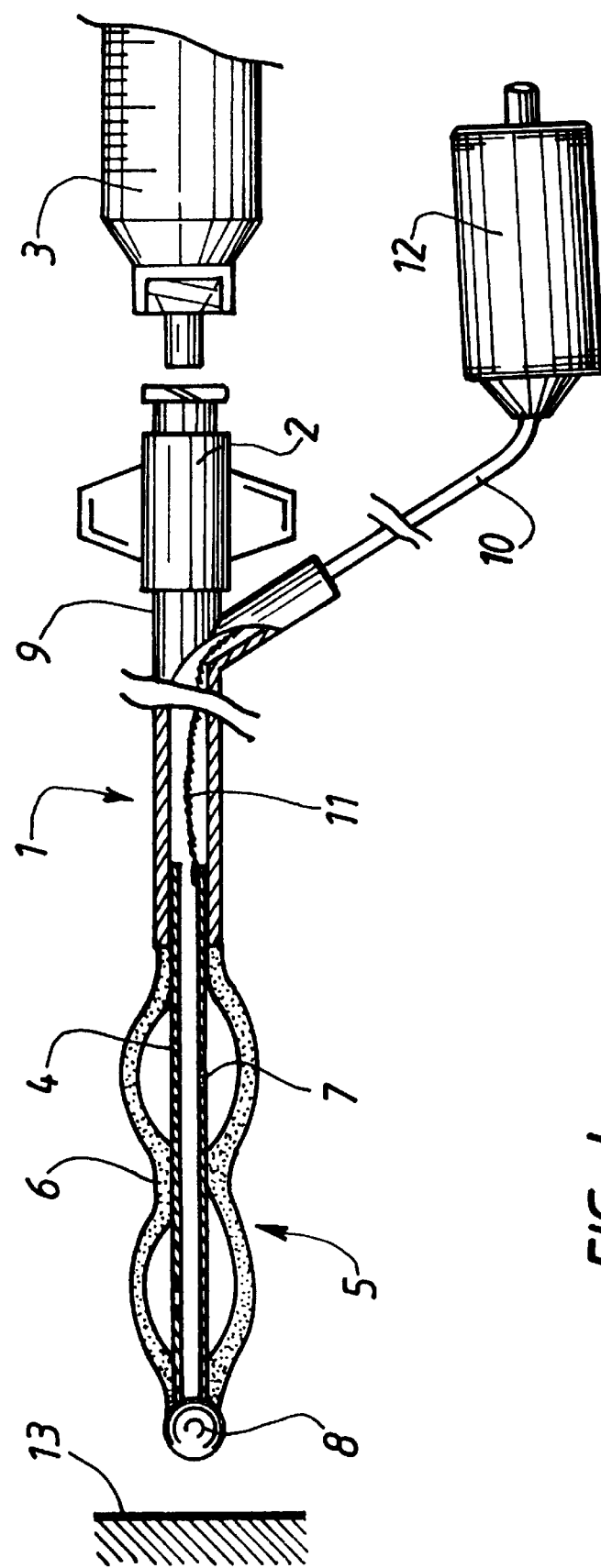

The following description of a particular embodiment of the invention is given by way of a non-limiting example, in reference to the appended schematic drawing of a catheter according to the invention which comprises a tubular body 1 equipped at its external end with an inflation connector 2. Here the connector 2 is equipped to receive the tip of a syringe 3.

At its other end, the body 1 is connected, for example by bonding, to a metal tube 4 made of stainless steel, the body and the tube being coaxial and the end of the tube being inserted into the end of the body.

A silicone balloon 5 covers the external surface of the tube 4. This balloon 5 is in fact tubular and both of its ends are impermeably bonded to the tube. The balloon 5 also comprises, in its center part, a diameter restriction 6 whose function will be explained below.

Furthermore, the tube 4 comprises in its wall inflation holes 7 through which the balloon can be inflated from the connector 2, the body 1 and the tube 4.

A sphere 8 is welded to the end of the tube 4, which it obturates on the far side of the balloon 5.

Near the connector 2, the body 1 forms a connection 9 into which an electrically conductive cable 10 opens in impermeable fashion. The conductive wire 11 of this cable 10 extends along the inside of the entire body 1 so as to end up being welded to the tube 4. The external end of the cable 10 is connected to a standard connector 12 for a single-pole electrocautery probe. Thus, the sphere 8 is electrically connected to the connector 12.

In order to pierce a membrane 13, the sphere 8 is first placed in contact with it, and then supplied with power from the connector 12. An opening having thus been produced in the membrane, the end of the catheter is inserted into it, until the membrane is situated at the level of the diameter restriction 6.

The balloon 5 is then inflated from the connector 2 in order to dilate the opening of the membrane. Because of the diameter restriction 6, the balloon cannot slip to one side of the membrane or the other, and therefore remains in place.

When the opening has reached a sufficient size, the balloon 5 is deflated and the catheter can be withdrawn.

What is claimed is:

1. A catheter for neurosurgery comprising a tubular body having a proximal end and a distal end, and having mounted on the distal end thereof a dilating balloon of elongated shape and comprising in a center part thereof a diameter restriction, said balloon having a proximal end which is mounted to the distal end of the tubular body and a distal end at which an electrocautery tip is disposed, said tubular body including means at the proximal end thereof for connecting to inflation means for the balloon, and internally comprising an electrical feed wire in electrical connection with the electrocautery tip.

2. The catheter according to claim 1, additionally comprising a metal tube having a proximal end and a distal end, in which the distal end of the tubular body coaxially supports the proximal end of the metal tube and the distal end of the metal tube comprises the electrocautery tip welded thereto, the feed wire being electrically connected to the metal tube, the metal tube further comprising a perforated wall around which the balloon is mounted, the perforated wall permitting the balloon to be inflated.

* * * * *